United States Patent [19]
Frey et al.

[11] Patent Number: 5,752,950
[45] Date of Patent: May 19, 1998

[54] SYSTEM FOR AUTOMATICALLY INHIBITING OPHTHALMIC TREATMENT LASER

[75] Inventors: Rudolph W. Frey, Orlando; Neil Zepkin, Casselberry; George Richard Downes, Jr., Orlando, all of Fla.

[73] Assignee: Autonomous Technologies Corp., Orlando, Fla.

[21] Appl. No.: 596,891

[22] Filed: Dec. 7, 1995

Related U.S. Application Data

[63] Continuation of Ser. No. 232,766, Apr. 25, 1994, abandoned.

[51] Int. Cl.$^6$ .................................................... A61N 5/06
[52] U.S. Cl. .................................. 606/12; 606/4; 606/5; 606/13
[58] Field of Search .......................... 606/2–4, 10–14, 606/18, 19; 607/88–92

[56] References Cited

U.S. PATENT DOCUMENTS

| | | | |
|---|---|---|---|
| 4,438,765 | 3/1984 | Wilinsky | 606/4 |
| 4,443,075 | 4/1984 | Crane | 606/18 |
| 4,702,245 | 10/1987 | Schroder et al. | 607/89 |
| 4,972,836 | 11/1990 | Schenck et al. | 606/4 |

*Primary Examiner*—David M. Shay

[57] ABSTRACT

A system is provided for use with an ophthalmic treatment laser that produces a treatment laser beam. The system automatically inhibits transmission of the treatment laser beam when a threshold amount of eye movement is detected. An eye movement sensor determines measurable amounts of eye movement such as saccadic eye movement. The eye movement sensor generates light energy that is eye safe, focuses the light energy on the eye, and detects energy reflected from the eye due to the incident light energy. The eye movement sensor determines the measurable amount of eye movement based on changes in the reflected energy. A dichroic beamsplitter is optically disposed between the ophthalmic treatment laser and the eye to direct the treatment laser beam to the eye. The beamsplitter is also optically disposed between the eye movement sensor and the eye to direct the sensor's light energy to the eye and the resulting reflected energy back to the sensor. When the measurable amount of eye movement exceeds the threshold amount, control logic outputs a treatment laser inhibit signal to the ophthalmic treatment laser.

13 Claims, 2 Drawing Sheets

SYSTEM FOR AUTOMATICALLY INHIBITING OPHTHALMIC TREATMENT LASER

This is a continuation of copending application Ser. No. 08/232,766 filed on Apr. 25, 1994 now abandoned.

This patent application is copending with related patent application entitled "Eye Movement Sensing Method and System" filed Apr. 25, 1994 as Ser. No. 08/232,990 as subject patent application and owned by the same assignee. The disclosure in that application is incorporated herein by reference.

FIELD OF THE INVENTION

The invention relates generally to ophthalmic laser surgery, and more particularly to a system used in conjunction with an ophthalmic treatment laser for automatically inhibiting the treatment laser upon the detection of a specified amount of eye movement.

BACKGROUND OF THE INVENTION

Photorefractive keratectomy (PRK) is a procedure for laser correction of focusing deficiencies of the eye by modification of corneal curvature. PRK is distinct from the use of laser-based devices for more traditional ophthalmic surgical purposes, such as tissue cutting or thermal coagulation. PRK is generally accomplished by use of a 193 nanometer wavelength excimer laser beam that ablates away corneal tissue in a photo decomposition process. Most clinical work to this point has been done with a laser operating at a fluence level of 120–195 mJ/cm$^2$ and a pulse-repetition rate of approximately 5–10 Hz. The procedure has been referred to as "corneal sculpting."

Before sculpting of the cornea takes place, the epithelium or outer layer of the cornea is mechanically removed to expose Bowman's membrane on the anterior surface of the stroma. At this point, laser ablation at Bowman's layer can begin. An excimer laser beam is preferred for this procedure. The beam may be variably masked during the ablation to remove corneal tissue to varying depths as necessary for recontouring the anterior stroma. Afterward, the epithelium rapidly regrows and resurfaces the contoured area, resulting in an optically correct (or much more nearly so) cornea. In some cases, a surface flap of the cornea is folded aside and the exposed surface of the cornea's stroma is ablated to the desired surface shape with the surface flap then being replaced.

Phototherapeutic keratectomy (PTK) is a procedure involving equipment functionally identical to the equipment required for PRK. The PTK procedure differs from PRK in that rather than reshaping the cornea, PTK used the excimer laser to treat pathological superficial corneal dystrophies, which might otherwise require cornial transplants.

In both of these procedures, surgical errors due to application of the treatment laser during unwanted eye movement can degrade the refractive outcome of the surgery. Eve movement or position is critical since the treatment laser's effectiveness depends on its being centered on the patient's theoretical visual axis which, practically speaking, is approximately the center of the patient's pupil. However, this visual axis is difficult to determine due in part to residual eye movement and involuntary eye movement known as saccadic eye movement. Saccadic eye movement is high-speed movement (i.e., of very short duration, 10–20 milliseconds, and typically up to 1° of eye rotation) inherent in human vision and is used to provide dynamic scene images to the retina. Saccadic eye movement, while being small in amplitude, varies greatly from patient to patient due to psychological effects, body chemistry, surgical lighting conditions, etc. Thus, even though a surgeon may be able to recognize some eye movement and can typically inhibit/restart a treatment laser by operation of a manual switch, the surgeon's reaction time is not fast enough to prevent application of the treatment laser during all unwanted eye movement.

SUMMARY OF THE INVENTION

Accordingly, it is an object of the present invention to provide a system for automatically inhibiting an ophthalmic treatment laser upon the detection of a specified amount of eye movement.

Another object of the present invention is to provide a system for inhibiting an ophthalmic treatment laser upon the detection of a specified amount of eye movement by sensing the eye movement in a non-intrusive fashion.

Still another object of the present invention is to provide a system for inhibiting an ophthalmic treatment laser in response to a specified amount of saccadic eye movement.

Other objects and advantages of the present invention will become more obvious hereinafter in the specification and drawings.

In accordance with the present invention, a system is provided for use with an ophthalmic treatment laser that produces a treatment laser beam. The system automatically inhibits transmission of the treatment laser beam to an eye when a threshold amount of eye movement is detected. An eye movement sensor determines measurable amounts of eye movement. The eye movement sensor includes a light source generating light energy that is eye safe, an optical delivery arrangement focusing the light energy on the eye, and an optical receiving arrangement detecting energy reflected from the eye due to the incident light energy. The eye movement sensor determines the measurable amount of eye movement based on changes in the reflected energy. A dichroic beamsplitter is optically disposed between the ophthalmic treatment laser and the eye to direct the treatment laser beam to the eye. The beamsplitter is also optically disposed between the eye movement sensor and the eye to direct the sensor's light energy to the eye and the reflected energy back to the sensor. Control logic outputs a treatment laser inhibit signal to the ophthalmic treatment laser when the measurable amount of eye movement exceeds the threshold amount. The treatment laser inhibit signal is used by the ophthalmic treatment laser to inhibit transmission of the treatment laser beam until the measurable amount of eye movement is less than the threshold amount.

DETAILED DESCRIPTION OF THE INVENTION

Figure 1:
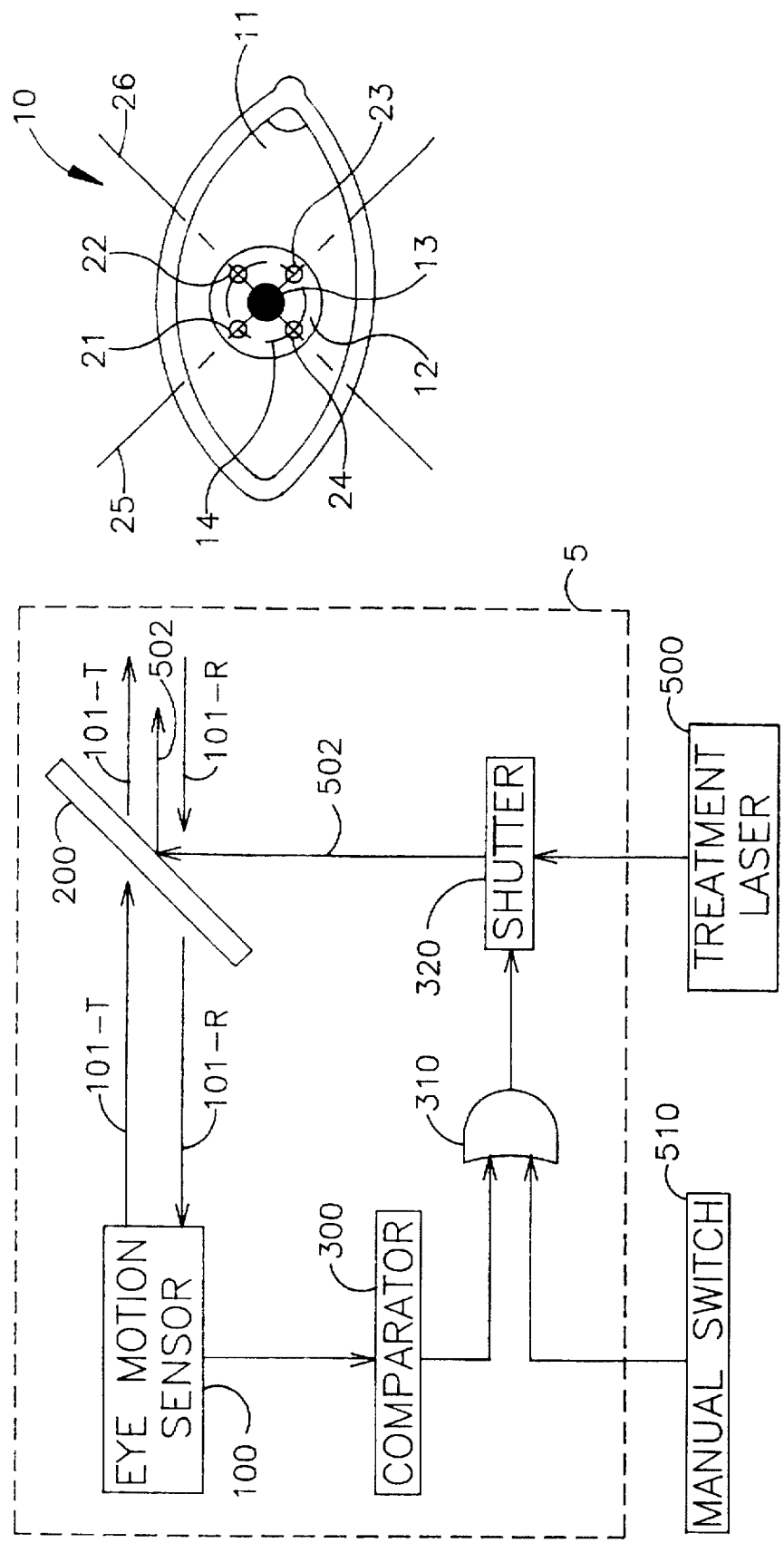
FIG. 1 is a block diagram of a system used in conjunction with an ophthalmic treatment laser for automatically inhibiting the treatment laser upon the detection of a specified amount of eye movement in accordance with the present invention.

Referring now to the drawings, and more particularly to FIG. 1, a block diagram is shown of a system, contained with the dotted line box designated by reference numeral 5, for automatically inhibiting transmission of a treatment laser beam 502 produced by an ophthalmic treatment laser 500. Such treatment lasers are well known in the art and can be used for a variety of surgical procedures. By way of example, it will be assumed that treatment laser beam 502 is a 193 nanometer wavelength excimer laser beam used in both PRK and PTK procedures.

System 5 includes an eye movement sensor 100, a dichroic beamsplitter 200 is of an optical configuration that reflects treatment laser beam 502 to eye 10 and passes light energies 101-T/101-R between sensor 100 and eye 10, and a control system that includes comparator 300, logical OR 310 and electromechanical shutter 320. In operation, treatment laser beam 502 is reflected toward eye 10 by way of dichroic beamsplitter 200. Beamsplitter 200 is configured to reflect light having wavelength associated with treatment laser beam 502. While treatment laser beam 502 is directed towards eye 10, sensor 100 determines the amount of eye movement. To do this, sensor 100 first transmits light energy 101-T to eye 10 by transmitting same through beamsplitter 200 (which has been selected to transmit such light energy). Light energy reflected from eye 10, as designated by reference numeral 101-R, passes back through beamsplitter 200 to sensor 100. Sensor 100 then determines the amount of eye movement based on the changes in reflection energy 101-R.

In order to take advantage of the transmission/reflection properties of beamsplitter 200, light energy 101-T must be of a different wavelength than that of treatment laser beam 502. Further, in view of the fact that the present invention is to be used in ophthalmic surgical procedures, the safety of light energy 101-T must be taken into consideration. In terms of PRK and PTK procedures, the light energy must be non-ablating with respect to the eye's corneal tissue. The light energy should preferably lie outside the visible spectrum so as not to interfere or obstruct a surgeon's view of the eye undergoing the surgical procedure. Further, the light energy must be "eye safe" to meet the American National Standards Institute (ANSI) safety requirements. These requirements are predicated on the type of light energy being used. While a variety of light wavelengths satisfy the above requirements, by way of example, light energy 101-T is infrared light energy in the 900 nanometer wavelength region. Light in this region meets the above noted criteria and is further produced by readily available, economically affordable light sources. One such light source is a high pulse repetition rate GaAs 905 nanometer laser operating at 4 kHz which produces an ANSI defined eye safe pulse of 10 nanojoules in a 50 nanosecond pulse.

Once determined, the amount of eye movement is compared with specified threshold value(s) at comparator 300. The threshold value(s) can be set by a surgeon based upon a variety of factors such as the particular surgical procedure, the particular patient's eye characteristics, lighting conditions, etc. The threshold value(s) can be in terms of horizontal vertical and/or angular movement.

If eye movement exceeds the threshold value(s), an inhibit signal is automatically passed to logical OR 310. Note that an inhibit signal might also originate from a manually operated switch 510 (e.g., typically, a foot switch operated by the surgeon). In either case, the inhibit signal is passed to treatment laser 500.

It is to be understood that "inhibiting" in the present invention may be achieved in a variety of manners. By way of example, the inhibit signal could control the state of electromechanical shutter 320 in order to block beam 502. A wade variety of shutters are commercially available that close within milliseconds of an electrical command. The advantage of shuttering beam 502 (as opposed to interrupting production of beam 502) is that treatment laser 500 remains operational thereby avoiding any performance anomalies associated with interrupting/resuming power to treatment laser 500.

When the inhibit signal ceases to be present (i.e., foot switch 510 is not engaged and the measured amount of eye movement is less than the specified threshold value), shutter 320 is electrically commanded to open by a change in the state of the inhibit signal. For example, shutter 320 could be configured to be a normally closed solenoid operated device such that an inhibit signal of 0 volts closes shutter 320 while an inhibit signal of 5 volts opens shutter 320.

Figure 2:
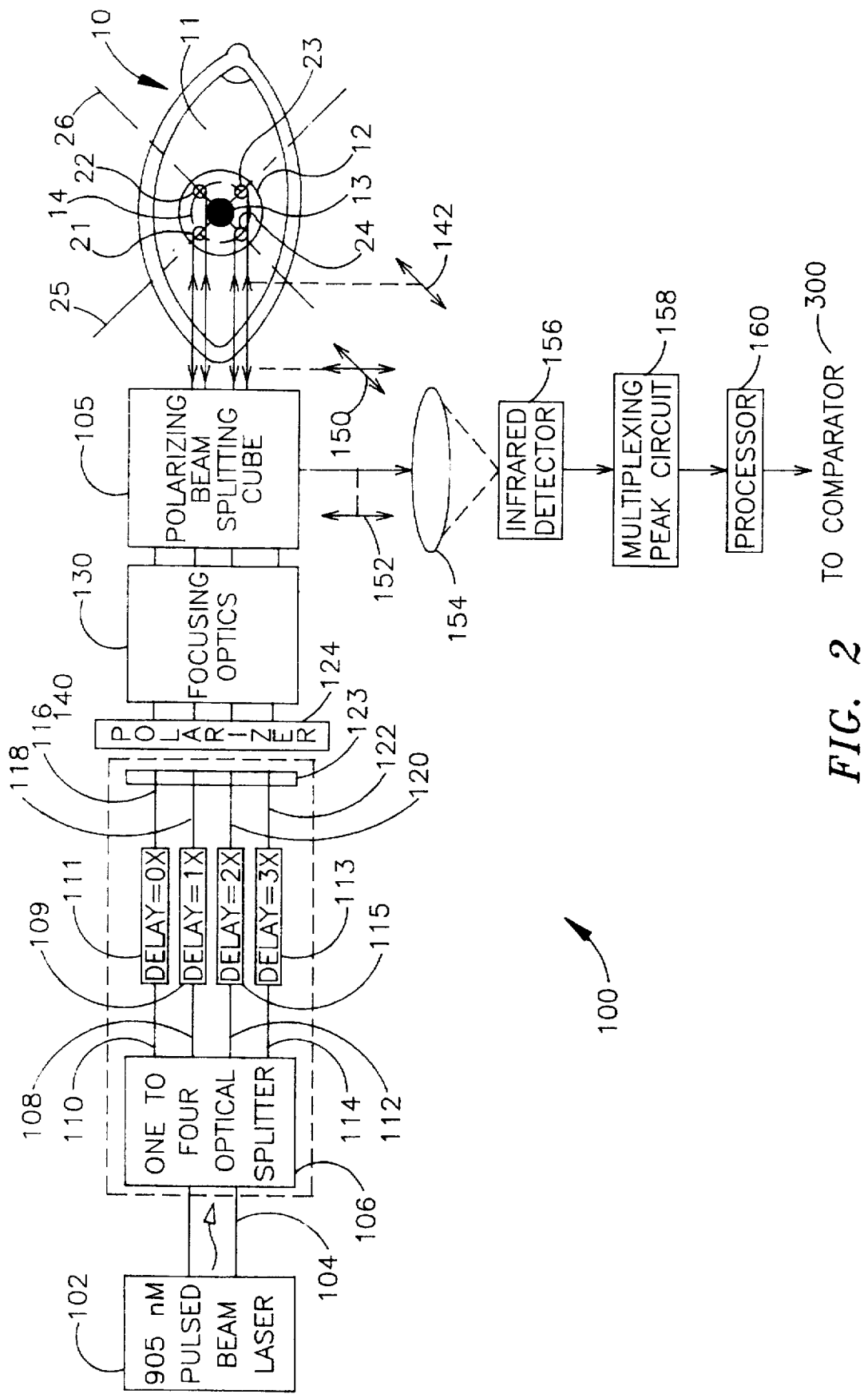
FIG. 2 is a block diagram of a preferred embodiment eye movement sensor.

A preferred embodiment method for determining the amount of eye movement, as well as eye movement sensor 100 for carrying out such a method, are described in detail in the aforementioned copending patent application. However, for purpose of a complete description, sensor 100 will be described briefly with the aid of the block diagram shown in FIG. 2. Sensor 100 may be broken down into a delivery portion and a receiving portion. Essentially, the delivery portion projects light energy 101-T in the form of light spots 21, 22, 23 and 24 onto a boundary (e.g., iris/pupil boundary 14) on the surface of eye 10. The receiving portion monitors light energy 101-R in the form of reflections caused by light spots 21, 22, 23 and 24.

In delivery, spots 21 and 23 are focused and positioned on axis 25 while spots 22 and 24 are focused and positioned on axis 26 as shown. Axes 25 and 26 are orthogonal to one another. Spots 21, 22, 23 and 24 are focused to be incident on and evenly spaced about iris/pupil boundary 14. The four spots 21, 22, 23 and 24 are of equal energy and are spaced evenly about and on iris/pupil boundary 14. This placement provides for two-axis motion sensing in the following manner. Each light spot 21, 22, 23 and 24 causes a certain amount of reflection at its position on iris/pupil boundary 14. Since boundary 14 moves in coincidence with eye movement, the amount of reflection from light spots 21, 22, 23 and 24 changes in accordance with eye movement. By spacing the four spots evenly about the circular boundary geometry, horizontal or vertical eye movement is detected by changes in the ratios between reflections from adjacent pairs of spots. For example, horizontal eye movement is monitored by comparing the combined reflection from light spots 21 and 24 with the combined reflection from light spots 22 and 23. In a similar fashion, vertical eye movement is monitored by comparing the combined reflection from light spots 21 and 22 with the combined reflection from light spots 23 and 24.

More specifically, the delivery portion includes a 905 nanometer pulsed diode laser 102 transmitting light through optical fiber 104 to an optical fiber assembly 105 that splits and delays each pulse from laser 102 into preferably four equal energy pulses. Assembly 105 includes one-to-four optical splitter 106 that outputs four pulses of equal energy into optical fibers 108, 110, 112, 114. In order to use a single processor to process the reflections caused by each pulse transmitted by fibers 108, 110, 112 and 114, each pulse is uniquely delayed by a respective fiber optic delay line 109, 111, 113 and 115. For example, delay line 109 causes a delay of zero, i.e., DELAY=0x where x is the delay increment; delay line 111 causes a delay of x, i.e., DELAY=1x; etc.

The pulse repetition frequency and delay increment x are chosen so that the data rate of sensor 100 is greater than the speed of the movement of interest. In terms of saccadic eye movement, the data rate of sensor 100 must be on the order of at least several hundred hertz. For example, a sensor data rate of approximately 4 kHz is achieved by 1) selecting a small but sufficient value for x to allow processor 160 to handle the data (e.g., 160 nanoseconds), and 2) selecting the time between pulses from laser 102 to be 250 microseconds (i.e., laser 102 is pulsed at a 4 kHz rate).

The four equal energy pulses exit assembly 105 via optical fibers 116, 118, 120 and 122 which are configured as a fiber optic bundle 123. Bundle 123 arranges the optical fibers such that the center of each fiber forms the corner of a square. Light from assembly 105 is passed through an optical polarizer 124 that outputs horizontally polarized light beams as indicated by arrow 126. Horizontally polarized light beams 126 pass to focusing optics 130 where spacing between beams 126 is adjusted based on the boundary of interest. Additionally, a zoom capability (not shown) can be provided to allow for adjustment of the size of the pattern formed by spots 21, 22, 23 and 24. This capability allows sensor 100 to adapt to different patients, boundaries, etc.

A polarizing beam splitting cube 140 receives horizontally polarized light beams 126 from focusing optics 130. Cube 140 is configured to transmit horizontal polarization and reflect vertical polarization. Accordingly, cube 140 transmits only horizontally polarized light beams 126 as indicated by arrow 142. Thus, it is only horizontally polarized light that is incident on eye 10 as spots 21, 22, 23 and 24. Upon reflection from eye 10, the light energy is depolarized (i.e., it has both horizontal and vertical polarization components) as indicated by crossed arrows 150.

The receiving portion first directs the vertical component of the reflected light as indicated by arrow 152.

Thus, cube 140 serves to separate the transmitted light energy from the reflected light energy for accurate measurement. The vertically polarized portion of the reflection from spots 21, 22, 23 and 24, is passed through focusing lens 154 for imaging onto an infrared detector 156. Detector 156 passes its signal to a multiplexing peak detecting circuit 158 which is essentially a plurality of peak sample and hold circuits, a variety of which are well known in the art. Circuit 158 is configured to sample (and hold the peak value from) detector 156 in accordance with the pulse repetition frequency of laser 102 and the delay x. For example, if the pulse repetition frequency of laser 102 is 4 kHz, circuit 158 gathers 15 reflections from spots 21, 22, 23 and 24 every 250 microseconds.

The values associated with the reflected energy for each group of four spots (i.e., each pulse of laser 102) are passed to a processor 160 where horizontal and vertical components of eye movement are determined. For example let $R_{21}$, $R_{22}$, $R_{23}$ and $R_{24}$ represent the detected amount of reflection from one group of spots 21, 22, 23 and 24, respectively. A quantitative amount of horizontal movement is determined directly from the normalized relationship $$\frac{(R_{21} + R_{24}) - (R_{22} + R_{23})}{R_{21} + R_{22} + R_{23} + R_{24}} \quad (1)$$

while a quantitative amount of vertical movement is determined directly from the normalized relationship $$\frac{(R_{21} + R_{22}) - (R_{23} + R_{24})}{R_{21} + R_{22} + R_{23} + R_{24}} \quad (2)$$

Note that normalizing (i.e., dividing by $R_{21}+R_{22}+R_{23}+R_{24}$) reduces the effects of variations in signal strength. Once determined, the measured amounts of eye movement are sent to comparator 300.

The advantages of the present invention are numerous. Unwanted eye movement is used to automatically trigger the inhibition of an ophthalmic treatment laser to eliminate unwanted corneal cutting or ablation. The system operates without interfering with the particular treatment laser or the surgeon performing the eye treatment procedure.

Although the invention has been described relative to a specific embodiment thereof, there are numerous variations and modifications that will be readily apparent to those skilled in the art in the light of the above teachings. It is therefore to be understood that, within the scope of the appended claims, the invention may be practiced other than as specifically described.

What is claimed as new and desired to be secured by Letters Patent of the United States is:

1. A system used in combination with an ophthalmic treatment laser that produces a treatment laser beam, said system automatically inhibiting transmission of said treatment laser beam to an eye when a threshold amount of eye movement is detected, said system comprising:

an eye movement sensor for determining a measurable amount of eye movement, said eye movement sensor including
1) a single light source for generating a light beam of light energy that is outside the visible spectrum and that is eye safe,
2) an optical delivery arrangement for converting said light beam into a plurality of separate light spots and for directing said plurality of separate light spots and for directing said plurality of separate light spots onto a corresponding plurality of positions located on said eye, said eye reflecting light energy from said plurality of spots with the amount of said energy changing with movement of said eye, said optical delivery arrangement including an arrangement for causing each of said spots to be uniquely identified by a delay arrangement for introducing a unique time delay as said unique identification into each of said plurality of light spots, and
3) a single detector optical receiving arrangement for detecting said light energy from each of said plurality of spots reflected from said eye for determining said measurable amount of eye movement based on changes in said reflected energy;

an opthalmic treatment laser;

an optical beamsplitter located on the optical path between said ophthalmic treatment laser and said eye for directing said treatment laser beam to said eye, and also located on the optical path between said eye movement sensor and said eye for directing said light energy to said eye and said reflected energy to said optical receiving arrangement; and control logic for outputting a treatment laser inhibit signal when said measurable amount of eye movement exceeds said threshold amount, wherein said treatment laser inhibit signal inhibits transmission of said treatment laser beam to said eye until said measurable amount of eye movement is less than said threshold amount.

2. A system as in claim 1 wherein said light source generates said light energy in the 900 nanometer wavelength region.

3. A system as in claim 1 wherein said optical beamsplitter comprises a dichroic beamsplitter having first and second sides, said first side receiving and reflecting said treatment laser beam to said eye, said second side receiving and transmitting said light energy to said eye, and said first side receiving and transmitting said reflected energy to said optical receiving arrangement.

4. A system as in claim 3 wherein said optical delivery arrangement includes:

means for polarizing said light energy into horizontally polarized components; and a polarization beam splitting cube for transmitting only said horizontally polarized components from said light energy to said dichroic beamsplitter.

5. A system as in claim 4 wherein said reflected energy is vertically and horizontally polarized, said single detector optical receiving arrangement including:

said polarization beam splitting cube for directing said reflected energy that is vertically polarized separately from said reflected energy that is horizontally polarized;

said single detector optical receiving arrangement measuring said reflected energy that is vertically polarized; and said control logic including a processor for determining said measurable amount of eye movement based on said reflected energy that is vertically polarized.

6. A system as in claim 1 wherein said optical delivery arrangement includes:

focusing optics for focusing said plurality of light spots on said corresponding plurality of positions located on a boundary whose movement is coincident with that of said eye movement, said boundary defined by two adjoining surfaces having different coefficients of reflection, wherein a portion of said reflected energy is reflected from each of said plurality of positions.

7. A system as in claim 6 wherein said optical delivery arrangement further includes zoom optics for adjusting the size of a pattern formed by said plurality of light spots incident on said corresponding plurality of positions.

8. A system as in claim 6 wherein said boundary is circular and said plurality of light spots comprises four light spots, said focusing optics including an arrangements for spacing said four light spots approximately evenly about said circular boundary.

9. A system as in claim 1 wherein said optical delivery arrangement includes:

a polarizer for polarizing said light energy into horizontally polarized components; and a polarization beam splitting cube for transmitting only said horizontally polarized components from said light energy to said optical beamsplitter.

10. A system as in claim 9 wherein said reflected energy is vertically and horizontally polarized, said single detector optical receiving arrangement including:

said polarization beam splitting cube for directing said reflected energy that is vertically polarized separately from said reflected energy that is horizontally polarized;

said single detector optical receiving arrangement measuring said reflected energy that is vertically polarized; and said control logic including a processor for determining said measurable amount of eye movement based on said reflected energy that is vertically polarized.

11. A system as in claim 1 wherein said optical delivery arrangement includes:

an optical splitter for converting said light energy into said plurality of light spots; and focusing optics for focusing said plurality of light spots on said corresponding plurality of positions located on a boundary whose movement is coincident with that of said eye movement, said boundary defined by two adjoining surfaces having different coefficients of reflection, wherein a portion of said reflected energy is reflected from each of said plurality of positions.

12. A system as in claim 14 wherein said boundary is circular and said plurality of light spots comprises four light spots, said focusing optics including an arrangement for spacing said four light spots approximately evenly about said circular boundary.

13. A system used in combination with an ophthalmic treatment laser that produces a treatment laser beam, said system automatically inhibiting transmission of said treatment laser beam to an eye when a threshold amount of eye movement is detected, said system comprising:

an ophthalmic treatment laser;

an eye movement sensor for determining a measurable amount of eye movement, said eye movement sensor including:

1) a single light source for generating a light beam of light energy that is outside the visible spectrum and that is eye safe, 2) an optical delivery arrangement for converting said light beam into a plurality of separate light spots and for directing said plurality of separate light spots onto a corresponding plurality of positions located on said eye, said eye reflecting light energy from said plurality of spots with the amount of said energy changing with movement of the eye, said optical delivery arrangement including an arrangement for causing each of said spots to be uniquely identified by a delay arrangement for introducing a unique time delay as said identification into each of said plurality of light spots; and control logic for outputting a treatment laser inhibit signal when said measurable amount of eye movement exceeds said threshold amount, wherein said treatment laser inhibit signal is used by said ophthalmic treatment laser to inhibit transmission of said treatment laser beam to said eye until said measurable amount of eye movement is less than said threshold amount.

* * * * *